United States Patent
Nie et al.

(10) Patent No.: US 12,415,992 B2
(45) Date of Patent: Sep. 16, 2025

(54) DIOXYGENASE MUTANTS AND USE THEREOF IN SYNTHESIZING (2S,3R)-3-HYDROXYPIPECOLIC ACID

(71) Applicant: Jiangnan University, Wuxi (CN)

(72) Inventors: Yao Nie, Wuxi (CN); Yan Xu, Wuxi (CN); Songyin Zhao, Wuxi (CN); Jiaojiao Guan, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 19/027,003

(22) Filed: Jan. 17, 2025

(65) Prior Publication Data

US 2025/0171748 A1 May 29, 2025

Related U.S. Application Data

(63) Continuation of application No. PCT/CN2024/096634, filed on May 31, 2024.

(30) Foreign Application Priority Data

Jun. 2, 2023 (CN) .......................... 202310652819.5

(51) Int. Cl.
| | | |
|---|---|---|
| *C12N 9/02* | (2006.01) | |
| *C12N 1/20* | (2006.01) | |
| *C12N 15/70* | (2006.01) | |
| *C12P 17/12* | (2006.01) | |
| *C12R 1/19* | (2006.01) | |

(52) U.S. Cl.
CPC ............. *C12N 9/0071* (2013.01); *C12N 1/20* (2013.01); *C12N 15/70* (2013.01); *C12P 17/12* (2013.01); *C12R 2001/19* (2021.05); *C12Y 114/11028* (2013.01)

(58) Field of Classification Search
CPC ........ C12N 9/0071; C12N 1/20; C12N 15/70; C12P 17/12; C12R 2001/19; C12Y 114/11028
See application file for complete search history.

(56) References Cited

U.S. PATENT DOCUMENTS

| | | | | |
|---|---|---|---|---|
| 9,790,527 | B2 * | 10/2017 | Chen ...................... | C12P 17/12 |
| 10,968,469 | B2 * | 4/2021 | Boenitz-Dulat ........ | C12P 17/12 |
| 10,982,245 | B2 * | 4/2021 | Kim ....................... | C12N 15/77 |
| 11,845,779 | B2 * | 12/2023 | Dal Peraro ...... | G01N 27/44791 |
| 2020/0199544 | A1 | 6/2020 | Hong et al. | |

OTHER PUBLICATIONS

"EXPASY: EC 1.14.11.28"; Enzyme classification description. Obtained from: enzyme.expasy.org/EC/1.14.11.28 (2 pages total) ( Year: 2025).*
"Mutant." Merriam-Webster.com Dictionary, Merriam-Webster, https://www.merriam-webster.com/dictionary/mutant. (Accessed May 22, 2025). 3 pages total. (Year: 2025).*
"Take." Merriam-Webster.com Dictionary, Merriam-Webster, https://www.merriam-webster.com/dictionary/take. Accessed May 23, 2025). 6 pages total. (Year: 2025).*
Guan, J. "Mining and characterization of Fe(II)/alpha-ketoglutarate-dependent dioxygenase and its synthesis of (2S,3R)-3-hydroxypipecolic acid", China's Outstanding Master's Degree Thesis Full-text Database (Electronic Journal), No. 5, May 15, 2024. On IDS filed Jan. 21, 2025 (Year: 2024).*
Guan,J. et al., "R97 at "Handlebar" Binding Mode in Active Pocket Plays an Important Role in Fe(II)/-Ketoglutaric Acid-Dependent Dioxygenase cis-P3H-Mediated Selective Synthesis of (2S,3R)-3-Hydroxypipecolic Acid", Molecules, vol. 28, Feb. 15, 2023.
Clifton, I.J. et al., "Structure of proline 3-hydroxylase Evolution of the family of 2-oxoglutarate dependent oxygenases", Eur. J. Biochem., vol. 268, Dec. 31, 2001.p. 6625-6636.
Shibasaki, T. et al., "Cloning of an isozyme of proline 3-hydroxylase and its purification from recombinant *Escherichia coli*", Biotechnology Letters, vol. 22, Dec. 31, 2000, p. 1967-1973.
Koketsu, K. et al., "Refined Regio- and Stereoselective Hydroxylation of I-Pipecolic Acid by Protein Engineering of I-Proline cis-4-Hydroxylase Based on the X-ray Crystal Structure", ACS Synth. Biol., vol. 4, Aug. 29, 2014, p. 383-392.
Smart, T.J. et.al., "Studies on the selectivity of proline hydroxylases reveal new substrates including bicycles", Bioorganic Chemistry, vol. 94, Oct. 28, 2019.
Mori, H. et.al., "Purification and Cloning of a Proline 3-Hydroxylase, a Novel Enzyme Which Hydroxylates Free L-Proline to cis-3-Hydroxy-L-Proline", Journal of Bacteriology, vol. 179, No. 18, Sep. 30, 1997. p. 5677-5683.
Guan Jiaojiao, "Mining and characterization of Fe(II)/alpha-ketoglutarate-dependent dioxygenase(2S, 3R)-3-hydroxypipecolic acid" China's Outstanding Master's Degree Thesis Full-text DatabaseJournal), No. 5, May 15, 2024.

* cited by examiner

Primary Examiner — Terry A McKelvey
Assistant Examiner — Andrew T Moehlman
(74) Attorney, Agent, or Firm — IPro, PLLC; Na Xu (57) ABSTRACT

By mutating arginine at position 97 and asparagine at position 43 of a wild type L-proline-3-hydroxylase, a mutated L-proline-3-hydroxylase is obtained. The mutated L-proline-3-hydroxylase comprises a variant of the wild-type L-proline-3-hydroxylase having SEQ ID NO:1, which comprises a substitution of the arginine corresponding to position 97 (R97) of SEQ ID NO:1 and a substitution of the asparagine corresponding to position 43 (N43) of SEQ ID NO:1; wherein the amino acid substituted into the mutated L-proline-3-hydroxylase at position R97 is methionine, and wherein the amino acid substituted into the mutated L-proline-3-hydroxylase at position N43 is selected from the group consisting of threonine (T), alanine (A), valine (V), serine(S), aspartic acid (D), and lysine (K).

8 Claims, 4 Drawing Sheets
Specification includes a Sequence Listing.

DIOXYGENASE MUTANTS AND USE THEREOF IN SYNTHESIZING (2S,3R)-3-HYDROXYPIPECOLIC ACID

REFERENCE TO SEQUENCE LISTING

The instant application contains a Sequence Listing in XML format as a file named "PC240006A.xml", created on 2025 Jan. 6, of 45,697 byte in size, and which is hereby incorporated by reference in its entirety.

TECHNICAL FIELD

The present disclosure belongs to the technical field of enzyme engineering and genetic engineering, and relates to dioxygenase mutants and use thereof in synthesizing (2S,3R)-3-hydroxypipecolic acid.

BACKGROUND

Pipecolic acid is a chiral cyclic non-protein amino acid and a homolog of proline. pipecolic acid is present in many natural and synthetic bioactive molecules. Its derivative, hydroxypipecolic acid, is widely distributed in nature and has been identified in some antibiotics, terpenoids, and alkaloids. In addition, hydroxypipecolic acid also serves as an important building block for the synthesis of chiral drugs and other fields. (2S,3R)-3-hydroxypipecolic acid has been demonstrated to form a precursor of tetrazole amine after being coupled with amine, which has significant antibacterial activity and strong cytotoxicity against P388 leukemia cells. In addition, (2S,3R)-3-hydroxypipecolic acid has been used as a building block in a biosynthetic pathway of GE81112, which acts as a translation inhibitor to inhibit the formation of transport initiation complex.

(2S,3R)-3-hydroxypipecolic acid can be synthesized in several ways, including enzymolysis after racemization, or diastereoselective method, which usually use natural or non-natural amino acids (such as serine and its derivatives, glutamic acid or proline), carbohydrates glyceraldehyde or D-glucose) or optically active α-hydroxycarboxylic acid/1, 2-aminoethanol/sulfoxides as precursors. However, the synthetic processes often involve hazardous and toxic chemicals, which can produce toxic by-products and cause environmental problems. Furthermore, they are associated with poor selectivity and high energy consumption. Comparatively, enzymatic synthesis has the characteristics of high catalytic efficiency, high selectivity, low energy consumption, and environmental friendliness, and is a more feasible alternative.

Few reports on the enzymatic production of (2S,3R)-3-hydroxypipecolic acid are available, among which Fe(II)/α-ketoglutarate-dependent dioxygenases are powerful and versatile biocatalysts, and are ideal candidates for industrial production. It is worth noting that only a few enzymes in the family have been identified as capable of catalyzing the conversion of L-pipecolic acid to (2S,3R)-3-hydroxypipecolic acid, including L-proline-3-hydroxylase from *Streptomyces* sp. strain TH1, L-proline-4-hydroxylase from *Sinorhizobium meliloti*, and GetF from *Streptomyces* sp. L-49973. Although wild-type L-proline-3-hydroxylase can specifically catalyze the conversion of L-pipecolic acid to (2S,3R)-3-hydroxypipecolic acid, it has the problem of low catalytic efficiency.

SUMMARY

In view of the defect of low catalytic efficiency that the wild-type L-proline-3-hydroxylase catalyzes the conversion of L-pipecolic acid to (2S,3R)-3-hydroxypipecolic acid, the present disclosure adopts an enzyme engineering method to improve the reactivity of L-proline-3-hydroxylase to unnatural substrate L-pipecolic acid. When a substrate concentration is 10 mM, a molar yield of (2S,3R)-3-hydroxypipecolic acid produced by catalyzing the conversion of L-pipecolic acid through the wild-type L-proline-3-hydroxylasec under crude enzyme conditions is 21.40%. Therefore, the catalytic activity of the L-proline-3-hydroxylase used in the present disclosure is modified by enzyme engineering, which leads to new findings for the study of enzymatic synthesis of (2S,3R)-3-hydroxypipecolic acid.

The present disclosure provides an L-proline-3-hydroxylase mutant with improved catalytic efficiency for L-pipecolic acid, the mutant is obtained by mutating amino acid at position 97 of the L-proline-3-hydroxylase whose starting amino acid sequence is shown in SEQ ID NO. 1, as well as by mutating amino acid at position 43 of the forward mutant R97M from the previous round of protein modification.

SEQ ID NO. 1 (amino acid sequence of the wild-type L-proline-3-hydroxylase):

MRSHILGRIELDQERLGRDLEYLATVPTVEEEYDEFSNGFWKNIPLYNA

SGGSEDRLYRDLEGSPAQPTKHAEQVPYLNEIITTVYNGERLQMARTRN

LKNAVVIPHRDFVELDRELDQYFRTHLMLEDSPLAFHSDDDTVIHMRAG

EIWFLDAAAVHSAVNFAEFSRQSLCVDLAFDGAFDEKEAFADATVYAPN

LSPDVRERKPFTKEREAGILALSGVIGRENFRDILFLLSKVHYTYDVHP

GETFEWLVSVSKGAGDDKMVEKAERIRDFAIGARALGERFSLTTW

The present disclosure further provides an L-proline-3-hydroxylase mutant, the L-proline-3-hydroxylase mutant is obtained by mutating arginine at position 97 and asparagine at position 43 of the L-proline-3-hydroxylase whose amino acid sequence is shown in SEQ ID NO. 1.

In one embodiment of the present disclosure, the L-proline-3-hydroxylase mutant is obtained by mutating arginine at position 97 of the L-proline-3-hydroxylase whose amino acid sequence is shown in SEQ ID NO. 1 to methionine, and mutating asparagine at position 43 of the L-proline-3-hydroxylase whose amino acid sequence is shown in SEQ ID NO. 1 to threonine; and the mutant is named R97M/N43T (amino acid sequence shown in SEQ ID NO. 4).

In one embodiment of the present disclosure, the L-proline-3-hydroxylase mutant is obtained by mutating arginine at position 97 of the L-proline-3-hydroxylase whose amino acid sequence is shown in SEQ ID NO. 1 to methionine, and mutating asparagine at position 43 of the L-proline-3-hydroxylase whose amino acid sequence is shown in SEQ ID NO. 1 to alanine; and the mutant is named R97M/N43A (amino acid sequence shown in SEQ ID NO. 5).

In one embodiment of the present disclosure, the L-proline-3-hydroxylase mutant is obtained by mutating arginine at position 97 of the L-proline-3-hydroxylase whose amino acid sequence is shown in SEQ ID NO. 1 to methionine, and mutating asparagine at position 43 of the L-proline-3-hydroxylase whose amino acid sequence is shown in SEQ ID NO. 1 to valine; and the mutant is named R97M/N43V (amino acid sequence shown in SEQ ID NO. 6).

In one embodiment of the present disclosure, the L-proline-3-hydroxylase mutant is obtained by mutating arginine at position 97 of the L-proline-3-hydroxylase whose amino acid sequence is shown in SEQ ID NO. 1 to methionine, and mutating asparagine at position 43 of the L-proline-3-hydroxylase whose amino acid sequence is shown in SEQ ID NO. 1 to serine; and the mutant is named R97M/N43S (amino acid sequence shown in SEQ ID NO. 7).

In one embodiment of the present disclosure, the L-proline-3-hydroxylase mutant is obtained by mutating arginine at position 97 of the L-proline-3-hydroxylase whose amino acid sequence is shown in SEQ ID NO. 1 to methionine, and mutating asparagine at position 43 of the L-proline-3-hydroxylase whose amino acid sequence is shown in SEQ ID NO. 1 to aspartic acid; and the mutant is named R97M/N43D (amino acid sequence shown in SEQ ID NO. 8).

In one embodiment of the present disclosure, the L-proline-3-hydroxylase mutant is obtained by mutating arginine at position 97 of the L-proline-3-hydroxylase whose amino acid sequence is shown in SEQ ID NO. 1 to methionine, and mutating asparagine at position 43 of the L-proline-3-hydroxylase whose amino acid sequence is shown in SEQ ID NO. 1 to lysine; and the mutant is named R97M/N43K (amino acid sequence shown in SEQ ID NO. 9).

The present disclosure further provides a gene encoding the L-proline-3-hydroxylase mutant above.

The present disclosure further provides a recombinant vector carrying the gene.

In one embodiment of the present disclosure, the recombinant vector includes but is not limited to pET-28a.

The present disclosure further provides a microbial cell expressing the L-proline-3-hydroxylase mutants, or carrying the gene or carrying the recombinant vector.

In one embodiment of the present disclosure, the microbial cell takes *Escherichia coli, Bacillus subtilis*, or yeast as a host cell.

In one embodiment of the present disclosure, the microbial cell takes bacteria or fungi as a host cell.

The present disclosure further provides a method for preparing (2S,3R)-3-hydroxypipecolic acid, where the method involves adding the L-proline-3-hydroxylase mutant or the microbial cell to a reaction system containing L-pipecolic acid, and (2S,3R)-3-hydroxypipecolic acid is prepared and obtained.

In one embodiment of the present disclosure, the method involves adding the L-proline-3-hydroxylase mutant or the microbial cell to a reaction system containing L-pipecolic acid, α-ketoglutaric acid, L-ascorbic acid and FeSO$_4$·7H$_2$O, and (2S,3R)-3-hydroxypipecolic acid is prepared and obtained.

In one embodiment, crude enzyme (100 μL) is added to a reaction system (150 μL), a final reaction system contains 10 mM substrate L-pipecolic acid, and a concentration of α-ketoglutaric acid should be greater than a concentration of the 10 mM substrate concentration of 10 mM, in which case, the concentration in a range of 15-30 mM can be selected. A concentration of the L-ascorbic acid should be greater than 0 mM, in which case, the concentration in a range of 10-20 mM can be selected. A concentration of FeSO$_4$·7H$_2$O should be kept at a lower level, in which case, the concentration in a range of 0-0.10 mM can be selected. A volume of the final reaction mixture is 250 μL, and the reaction is carried out at 10° C., pH 6.5 for 12 hours.

In one embodiment of the present disclosure, reaction conditions are as follows: crude enzyme (100 μL) is added to a reaction system (150 μL), a final reaction system contains 10 mM substrate L-pipecolic acid, 30 mM α-ketoglutaric acid, 15 mM L-ascorbic acid, 0.05 mM FeSO$_4$·7H$_2$O, the final reaction mixture system had a volume of 250 μL, and reaction was carried out for 12 hours at a temperature of 10° C. and pH of 6.5.

The present disclosure further provides a method for improving catalytic activity of L-proline-3-hydroxylase to substrate L-pipecolic acid, and the method is as follows: the L-proline-3-hydroxylase mutant involves mutating arginine at position 97 and asparagine at position 43 of the L-proline-3-hydroxylase whose amino acid sequence is shown in SEQ ID NO. 1.

In one embodiment of the present disclosure, the method includes mutating arginine at position 97 of the L-proline-3-hydroxylase whose amino acid sequence is shown in SEQ ID NO. 1 to methionine, and mutating asparagine at position 43 thereof to threonine at the same time.

In one embodiment of the present disclosure, the method includes mutating arginine at position 97 of the L-proline-3-hydroxylase whose amino acid sequence is shown in SEQ ID NO. 1 to methionine, and mutating asparagine at position 43 thereof to alanine at the same time.

In one embodiment of the present disclosure, the method includes mutating arginine at position 97 of the L-proline-3-hydroxylase whose amino acid sequence is shown in SEQ ID NO. 1 to methionine, and mutating asparagine at position 43 thereof to valine at the same time.

In one embodiment of the present disclosure, the method includes mutating arginine at position 97 of the L-proline-3-hydroxylase whose amino acid sequence is shown in SEQ ID NO. 1 to methionine, and mutating asparagine at position 43 thereof to serine at the same time.

In one embodiment of the present disclosure, the method includes mutating arginine at position 97 of the L-proline-3-hydroxylase whose amino acid sequence is shown in SEQ ID NO. 1 to methionine, and mutating asparagine at position 43 thereof to aspartic acid at the same time.

In one embodiment of the present disclosure, the method includes mutating arginine at position 97 of the L-proline-3-hydroxylase whose amino acid sequence is shown in SEQ ID NO. 1 to methionine, and mutating asparagine at position 43 thereof to lysine at the same time.

The present disclosure further provides the L-proline-3-hydroxylase mutant, or the gene, or the recombinant vector, or the use of the recombinant cell in the preparation of (2S,3R)-3-hydroxypipecolic acid or a product containing (2S,3R)-3-hydroxypipecolic acid; and the use involves: adding the L-proline-3-hydroxylase mutant or the recombinant L-proline-3-hydroxylase mutant expressed by microbial cells to a reaction system containing L-pipecolic acid, to prepare and obtain the (2S,3R)-3-hydroxypipecolic acid.

The present disclosure further provides a method for constructing the L-proline-3-hydroxylase mutant above, the method includes the following steps:
(1) according to sequence information of the L-proline-3-hydroxylase from *Streptomyces* sp. strain TH1 disclosed in the NCBI database, performing codon optimization based on codon preference rules of *Escherichia coli* to obtain an optimized gene of L-proline-3-hydroxylase; connecting the optimized gene of L-proline-3-hydroxylase into an expression vector pET28a to construct an L-proline-3-hydroxylase expression vector;
(2) using genes (involved in site-directed saturation mutagenesis) synthesized by GENCEFE Biotech to prepare an expression vector containing the L-proline-3-hydroxylase mutant;
(3) transforming the above vectors into BL21 engineering bacteria by chemical transformation to express each enzyme protein; culturing the strain in a test tube at 37° C. shaker overnight, transferring the same to an LB liquid culture medium containing 50 mg·L$^{-1}$ kanamycin at a 2% inoculation rate, culturing at 37° C. for 2-2.5 hours, and then adding IPTG with a concentration of 0.10 mM to adjust a temperature to 17° C. and culturing for 16 hours;

(4) centrifuging at 8000 r·min$^{-1}$ for 5 minutes and collecting bacterial pellets, disrupting cells through an ultrasonic disruption method, centrifuging in a refrigerated centrifuge at 12000 r·min$^{-1}$ for 30 minutes to collect supernatant, directly using the supernatant for crude enzyme reaction to explore changes in molar yield under crude enzyme conditions; or purifying the supernatant with a nickel column, and enzymatic properties such as enzyme activity and kinetic parameters of the pure L-proline-3-hydroxylase can be determined. Specifically, the enzyme activity is detected using an Fmoc-Cl pre-column derivatization method, and analyzed by high-performance liquid chromatography (HPLC). The kinetic parameters ($K_m$ and $V_{max}$) are measured in a standard enzyme activity assay system, with three separate measurements. Data are fitted to a Michaelis-Menten model using GraphPad Prism, and a protein concentration is kept at 0.50 mg·mL-1 during the measurements.

The present disclosure further provides a method for improving the enzymatic activity of L-proline-3-hydroxylase, the method includes: mutating arginine at position 97 of the L-proline-3-hydroxylase whose amino acid sequence is shown in SEQ ID NO. 1 to methionine, and mutating asparagine at position 43 thereof to threonine at the same time; or mutating arginine at position 97 of the L-proline-3-hydroxylase whose amino acid sequence is shown in SEQ ID NO. 1 to methionine, and mutating asparagine at position 43 thereof to alanine at the same time; or mutating arginine at position 97 of the L-proline-3-hydroxylase whose amino acid sequence is shown in SEQ ID NO. 1 to methionine, and mutating asparagine at position 43 thereof to valine at the same time; or mutating arginine at position 97 of the L-proline-3-hydroxylase whose amino acid sequence is shown in SEQ ID NO. 1 to methionine, and mutating asparagine at position 43 thereof to serine at the same time; or mutating arginine at position 97 of the L-proline-3-hydroxylase whose amino acid sequence is shown in SEQ ID NO. 1 to methionine, and mutating asparagine at position 43 thereof to aspartic acid at the same time; or mutating arginine at position 97 of the L-proline-3-hydroxylase whose amino acid sequence is shown in SEQ ID NO. 1 to methionine, and mutating asparagine at position 43 thereof to lysine at the same time.

Beneficial Effects (1) The specific activity of the L-proline-3-hydroxylase mutant R97M/N43T in the present disclosure is improved. 100 μL of pure enzyme is added to a 150 μL reaction mixture, the final reaction conditions are as follows: 10 mM L-pipecolic acid, 10 mM 2-OG (α-ketoglutaric acid, known as 2-oxoglutaric acid), 10 mM Vc (Vitamin C, known as L-Ascorbic acid), 1 mM $FeSO_4·7H_2O$, and 50 mM MES buffer (pH 6.5); the reaction is carried out on a metal oscillator at 17° C. and 1000 r·min$^{-1}$ for 15 minutes. The specific activity of R97M/N43T is 0.46 μmol·min$^{-1}$·mg$^{-1}$, which is 2.42 times that of R97M and 3.83 times that of the wild-type (WT) enzyme.

(2) The mutant R97M/N43T in the present disclosure is successfully optimized under given conditions. The reaction conditions (temperature and pH) and concentrations of reaction components ($Fe^{2+}$, 2-OG, and Vc) are optimized under crude enzyme conditions. R97M/N43T has low activity at higher temperatures, slightly acidic environments, and high concentrations of $Fe^{2+}$; the reaction is not completely dependent on exogenous $Fe^{2+}$, but is dependent on 2-OG; and the concentration of 2-OG required for the reaction exceeds that of the substrate, and the addition of Vc promotes the reaction.

(3) When a concentration of L-Pip is 10 mM and are under the optimal conditions, the molar yield of (2S,3R)-3-hydroxypipecolic acid catalyzed by R97M/N43T reaches 88%, which is 4.11 times that of the wild-type enzyme, in which case, the yield of (2S,3R)-3-hydroxypipecolic acid is 1278 mg·L$^{-1}$.

DETAILED DESCRIPTIONS OF THE EMBODIMENTS

Culture media and solutions involved in the following examples are as follows:

LB liquid culture medium (mg·mL$^{-1}$): yeast extract 5, tryptone 10, NaCl 10.

LB solid culture medium (mg·mL$^{-1}$): yeast extract 5, tryptone 10, NaCl 10, agar powder 15.

Protein purification Solution A: 20 mM Tris-HCl, 150 mM NaCl, adjusting pH to 7.5 and 8.0 with hydrochloric acid.

Protein purification Solution B: 20 mM Tris-HCl, 150 mM NaCl, IM imidazole, adjusting pH to 7.5 and 8.0 with hydrochloric acid.

Low-salt buffer: 20 mM Tris-HCl, 100 mM NaCl, adjusting pH to 7.5 with hydrochloric acid.

Protein gel staining solution: for a total volume of 1000 mL of protein gel staining solution, weighing 1 g of Coomassie Brilliant Blue R250, adding 450 mL of ethanol, 100 ml of acetic acid, and 450 mL of deionized water, and mixing thoroughly.

Protein gel destaining solution: for a total volume of 1000 mL of protein gel staining solution, adding 100 mL of ethanol, 100 mL of acetic acid, and 800 mL of deionized water, and mixing thoroughly.

Detection methods involved in the following examples are as follows:

Detection of content of (2S,3R)-3-hydroxypipecolic acid:

A sample is pipetted and centrifuged, supernatant is then collected and diluted to 4-7 mM, 125 µL of the sample is taken, 125 µL of 200 mM boric acid buffer (pH 9.2) is added to the sample, 250 µL of 10 mM Fmoc-Cl is then added, and shaken well and reacted for 15 minutes, 250 µL of 40 mM 1-aminoadamantane is added to terminate the reaction, filtering is performed using a 0.22 µm organic filter for detection and analysis. Detection conditions: a Diomansil C18 column (4.60 mm×250 mm×5 µm) is used, with a ultraviolet detection wavelength of 263 nm, a temperature of 25° C., a flow rate of 1 mL·min$^{-1}$, and a sample injection volume of 10 µL. A gradient elution method is adopted, a mobile phase A is 50 mM sodium acetate-glacial acetic acid buffer, pH 4.2; a mobile phase B is acetonitrile; Gradient program: Buffer A: 0-19 min 70%; 19-19.50 min 20%; 19.50-23.50 min 0%; 23.50-28 min 70%. Since a molecular weight of (2S,5S)-5-hydroxypipecolic acid is consistent with that of (2S,3R)-3-hydroxypipecolic acid, and a standard solution for quantification is prepared from (2S,5S)-5-hydroxypipecolic acid.

Calculation method for molar yield: when the reaction is performed with using 10 mM substrate L-Pip, a product (2S,3R)-3-hydroxypipecolic acid has a theoretical molar yield of 10 mM. An actual product generated is detected using the detection method for (2S,3R)-3-hydroxypipecolic acid content described above. Molar yield (%)=(Actual yield/Theoretical yield)×100.

A preparation methods for competent cells involved in the following examples is as follows:

Preparation of competent cells: competent cells are prepared according to instructions in the Competent Cell Preparation Kit (purchased from TaKaRa Bio Inc.), a single colony of *Escherichia coli* on a non-Kanamycin resistant LB plate is picked up and transferred into an LB tube, and cultured overnight at 37° C. and 200 r·min$^{-1}$ for 8-12 hours; the single colony is then transferred with an inoculation volume of 2% to a 250 mL triangular flask containing 50 mL LB culture medium, and cultured at 37° C. and 200 r·min$^{-1}$ until OD$_{600}$ reaches approximately 0.6-0.8, the triangular flask is placed on ice for 30 minutes; 50 mL of bacterial solution is aliquoted and transferred into two 50 mL sterilized centrifuge tubes (25 mL per tube) on a clean bench, the solution is centrifuged at 6000 r·min$^{-1}$ for 5 minutes at 4° C., a supernatant is discarded; and 10% Solution A is added to gently to resuspend a bacterial pellet, the solution is centrifuged again at 6000 r·min$^{-1}$ for 5 minutes at 4° C., a supernatant is discarded, 10% Solution B is added to gently to resuspend a bacterial pellet, 100 µL of bacterial solution is aliquoted and transferred into 1.5 mL sterilized EP tubes, which are stored at −80° C. for up to one year. All operations should be performed under sterile conditions.

A preparation method involved in the following examples is as follows:

Chemical transformation: competent medium is thawed on ice, 10 µL of recombinant plasmid is added on a clean bench and gently mixed and incubated on ice for 30 minutes around; heat shock is performed at 42° C. in a metal bath for 90 seconds to obtain a mixture, the mixture is placed on ice for 5 minutes, 800 µL of LB culture medium is added and cultured at 37° C. and 200 r·min$^{-1}$ for 1 hour, centrifugation is performed at 6000 r·min$^{-1}$ for 5 minute, and a supernatant is discarded on a clean bench; the remaining culture medium is resuspended and spread on a kanamycin-resistant plate, and cultured overnight at 37° C. for 12 hours, and colonies are picked up for colony PCR verification and sent to a sequencing company for sequencing.

Example 1: Construction of Recombinant Bacteria Containing L-Proline-3-Hydroxylase Mutants Specific steps were as follows:

(1) Construction of an Expression Vector and Recombinant Bacteria Containing Wild-Type L-Proline-3-Hydroxylase (Cis-P3H)

Sequence information of the L-proline-3-hydroxylase (SEQ ID NO. 1) was codon-optimized according to codon preference rules of *Escherichia coli* to obtain an optimized gene of L-proline-3-hydroxylase; the optimized gene of L-proline-3-hydroxylase was then inserted into an expression vector pET28a to construct an L-proline-3-hydroxylase (cis-P3H) expression vector pET28a (+)-cis-P3H, and wild-type recombinant bacteria *Escherichia coli* BL21 pET28a (+)-cis-P3H was obtained.

A PCR system: 25 µL PrimeSTARR MAX DNA Polymerase, 23 µL ddH$_2$O, 1 µL pET28a (+)-cis-P3H, 0.50 µL primer 1, 0.50 µL primer 2.

PCR reaction conditions: 98° C. for 30 second, 98° C. for 10 second, 55° C. for 5 second, 72° C. for 90 second, for a total of 30 cycles.

(2) Construction of an Expression Vector and Recombinant Bacteria Containing L-Proline-3-Hydroxylase Mutants Long and short fragments of the PCR product were ligated via homologous recombinase and then transformed into competent cells of *Escherichia coli* BL21 (DE3), and specific operations were the same as the chemical transformation method above.

Figure 6:
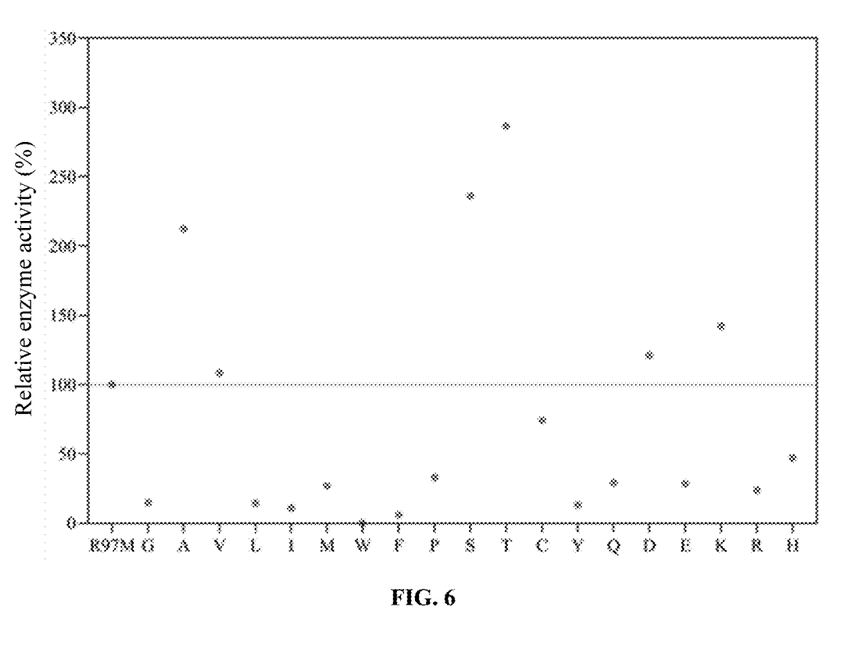
FIG. 6 shows iterative mutation results of N43 using R97M as a template.

Below was primer information (Table 1) of each mutant obtained by performing N43 saturation mutagenesis, taking R97M as a template (FIG. 6).

TABLE 1

Primer information of R97M and each mutant for N43 saturation mutagenesis using R97M as a template

| Different mutants | Primer sequence |
|---|---|
| pET28a(+)-R97M | F: tgaacgtctgcaaatggcgcgtaccatgaacctgaaaaacgctgttgttat(SEQ ID NO. 10)<br>R: ataacaacagcgttttcaggttcatggtacgcgccatttgcagacgttca(SEQ ID NO. 11) |
| pET28a(+)-R97M/N43G | F: tgagttcagcaacggtttctggaaaggcatcccgctgtacaacgcgagcgg(SEQ ID NO. 12)<br>R: ccgctcgcgttgtacagcgggatgcctttccagaaaccgttgctgaactca(SEQ ID NO. 13) |
| pET28a(+)-R97M/N43A | F: tgagttcagcaacggtttctggaaagcgatcccgctgtacaacgcgagcgg(SEQ ID NO. 14)<br>R: ccgctcgcgttgtacagcgggatcgctttccagaaaccgttgctgaactca(SEQ ID NO. 15) |
| pET28a(+)-R97M/N43V | F: tgagttcagcaacggtttctggaaagttatcccgctgtacaacgcgagcgg(SEQ ID NO. 16)<br>R: ccgctcgcgttgtacagcgggataactttccagaaaccgttgctgaactca(SEQ ID NO. 17) |
| pET28a(+)-R97M/N43L | F: tgagttcagcaacggtttctggaaactgatcccgctgtacaacgcgagcgg(SEQ ID NO. 18)<br>R: ccgctcgcgttgtacagcgggatcagtttccagaaaccgttgctgaactca(SEQ ID NO. 19) |
| pET28a(+)-R97M/N43I | F: gagttcagcaacggtttctggaaaatcatcccgctgtacaacgcgagcggt(SEQ ID NO. 20)<br>R: accgctcgcgttgtacagcgggatgattttccagaaaccgttgctgaactc(SEQ ID NO. 21) |
| pET28a(+)-R97M/N43M | F: gagttcagcaacggtttctggaaaatgatcccgctgtacaacgcgagcggt(SEQ ID NO. 22)<br>R: accgctcgcgttgtacagcgggatcattttccagaaaccgttgctgaactc(SEQ ID NO. 23) |
| pET28a(+)-R97M/N43W | F: tgagttcagcaacggtttctggaaatggatcccgctgtacaacgcgagcgg(SEQ ID NO. 24)<br>R: ccgctcgcgttgtacagcgggatccatttccagaaaccgttgctgaactca(SEQ ID NO. 25) |
| pET28a(+)-R97M/N43F | F: tgagttcagcaacggtttctggaaattcatcccgctgtacaacgcgagcgg(SEQ ID NO. 26)<br>R: ccgctcgcgttgtacagcgggatgaatttccagaaaccgttgctgaactca(SEQ ID NO. 27) |
| pET28a(+)-R97M/N43P | F: tgagttcagcaacggtttctggaaaccgatcccgctgtacaacgcgagcgg(SEQ ID NO. 28)<br>R: ccgctcgcgttgtacagcgggatcggtttccagaaaccgttgctgaactca(SEQ ID NO. 29) |
| pET28a(+)-R97M/N43S | F: gagttcagcaacggtttctggaaaagcatcccgctgtacaacgcgagcggt(SEQ ID NO. 30)<br>R: accgctcgcgttgtacagcgggatgctttccagaaaccgttgctgaactc(SEQ ID NO. 31) |
| pET28a(+)-R97M/N43T | F: gagttcagcaacggtttctggaaaaccatcccgctgtacaacgcgagcggt(SEQ ID NO. 32)<br>R: accgctcgcgttgtacagcgggatggttttccagaaaccgttgctgaactc(SEQ ID NO. 33) |
| pET28a(+)-R97M/N43C | F: tgagttcagcaacggtttctggaaatgcatcccgctgtacaacgcgagcgg(SEQ ID NO. 34)<br>R: ccgctcgcgttgtacagcgggatgcatttccagaaaccgttgctgaactca(SEQ ID NO. 35) |
| pET28a(+)-R97M/N43Y | F: tgagttcagcaacggtttctggaaatacatcccgctgtacaacgcgagcgg(SEQ ID NO. 36)<br>R: ccgctcgcgttgtacagcgggatgtatttccagaaaccgttgctgaactca(SEQ ID NO. 37) |
| pET28a(+)-R97M/N43Q | F: tgagttcagcaacggtttctggaaacagatcccgctgtacaacgcgagcgg(SEQ ID NO. 38)<br>R: ccgctcgcgttgtacagcgggatctgtttccagaaaccgttgctgaactca(SEQ ID NO. 39) |
| pET28a(+)-R97M/N43D | F: tgagttcagcaacggtttctggaaagacatcccgctgtacaacgcgagcgg(SEQ ID NO. 40)<br>R: ccgctcgcgttgtacagcgggatgtctttccagaaaccgttgctgaactca(SEQ ID NO. 41) |
| pET28a(+)-R97M/N43E | F: tgagttcagcaacggtttctggaaagaaatcccgctgtacaacgcgagcgg(SEQ ID NO. 42)<br>R: ccgctcgcgttgtacagcgggatttctttccagaaaccgttgctgaactca(SEQ ID NO. 43) |
| pET28a(+)-R97M/N43K | F: agttcagcaacggtttctggaaaaaaatcccgctgtacaacgcgagcggtg(SEQ ID NO. 44)<br>R: caccgctcgcgttgtacagcgggattttttccagaaaccgttgctgaact(SEQ ID NO. 45) |
| pET28a(+)-R97M/N43R | F: tgagttcagcaacggtttctggaaacgtatcccgctgtacaacgcgagcgg(SEQ ID NO. 46)<br>R: ccgctcgcgttgtacagcgggatacgtttccagaaaccgttgctgaactca(SEQ ID NO. 47) |
| pET28a(+)-R97M/N43H | F: tgagttcagcaacggtttctggaaacacatcccgctgtacaacgcgagcgg(SEQ ID NO. 2)<br>R: ccgctcgcgttgtacagcgggatgtgtttccagaaaccgttgctgaactca(SEQ ID NO. 3) |

Expression vectors and recombinant bacteria containing different mutants were prepared; and the recombinant bacteria were: E. coli BL21/pET28a (+)-R97M, E. coli BL21/pET28a (+)-R97M/N43G, E. coli BL21/pET28a (+)-R97M/N43A, E. coli BL21/pET28a (+)-R97M/N43V, E. coli BL21/pET28a (+)-R97M/N43L, E. coli BL21/pET28a (+)-R97M/N43I, E. coli BL21/pET28a (+)-R97M/N43M, E. coli BL21/pET28a (+)-R97M/N43W, E. coli BL21/pET28a (+)-R97M/N43F, E. coli BL21/pET28a (+)-R97M/N43P, E. coli BL21/pET28a (+)-R97M/N43S, E. coli BL21/pET28a (+)-R97M/N43T, E. coli BL21/pET28a (+)-R97M/N43C, E. coli BL21/pET28a (+)-R97M/N43Y, E. coli BL21/pET28a (+)-R97M/N43Q, E. coli BL21/pET28a (+)-R97M/N43D, E. coli BL21/pET28a (+)-R97M/N43E, E. coli BL21/pET28a (+)-R97M/N43K, E. coli BL21/pET28a (+)-R97M/N43R, E. coli BL21/pET28a (+)-R97M/N43H.

Example 2: Expression and Purification of L-Proline-3-Hydroxylase Mutants (1) Expression of L-Proline-3-Hydroxylase Mutants
1) The wild-type recombinant bacteria *Escherichia coli* BL21/pET28a (+)-cis-P3H and the recombinant bacteria containing mutants were inoculated into 5 mL LB medium containing kanamycin (50 µg·mL$^{-1}$) respectively and cultured at 37° C. and 200 r·min$^{-1}$ for 8-12 hours to prepare seed solutions;

2) the seed solutions were then transferred to 50 mL LB medium containing 50 µg·mL$^{-1}$ kanamycin at an inoculation amount of 2% (volume fraction), and cultured at 37° C. and 200 r min-1 until the OD$_{600}$ reached 0.6-0.8; and 0.10 mM IPTG was added to induce expression of the recombinant protein at 17° C. for 16 hours, and fermentation broths were then prepared respectively;

3) the fermentation broths were centrifuged at 8000 r·min$^{-1}$ for 15 minutes at 4° C. to collect bacterial pellets, respectively, and the bacterial pellets were washed twice with saline for subsequent use; and 4) the recombinant bacterial pellets were resuspended in 20 mM Tris-HCl (pH 7.5) buffer, cells containing a target plasmid were sonicated using an ultrasonic cell disruptor at 400 W power, with 2-second operation and 3-second interval. Cell lysate was centrifuged in a refrigerated centrifuge for 15 minutes to remove cell debris, with a centrifugation temperature set at 4° C. and a rotation speed at 10,000 r·min$^{-1}$ to prepare crude enzyme solutions containing different mutants, respectively.

Figure 1:
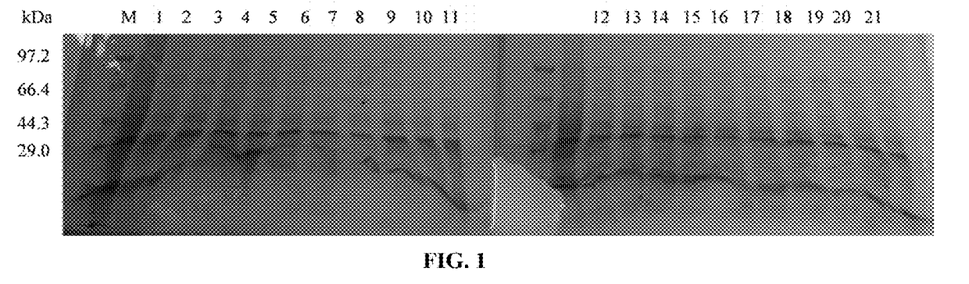
FIG. 1 shows expression verification of a saturated mutant library of N43 using R97M as a template, where M represents protein Marker; 1 represents a soluble fraction of *E. coli* BL21 (DE3); 2 represents *E. coli* BL21/pET28a (+)-R97M (33.15 kDa); 3 represents R97M/N43G; 4 represents R97M/N43A; 5 represents R97M/N43V; 6 represents R97M/N43L; 7 represents R97M/N43I; 8 represents R97M/N43M; 9 represents R97M/N43W; 10 represents R97M/N43F; 11 represents R97M/N43P; 12 represents R97M/N43S; 13 represents R97M/N43T; 14 represents R97M/N43C; 15 represents R97M/N43Y; 16 represents R97M/N43Q; 17 represents R97M/N43D; 18 represents R97M/N43E; 19 represents R97M/N43K; 20 represents R97M/N43R; 21 represents R97M/N43H.

Results indicated that all recombinant proteins were heterologously expressed in a soluble form. SDS-PAGE analysis of the soluble components of the recombinant proteins indicated that bands were consistent with a predicted molecular weight (FIG. 1).

(2) Purification of L-Proline-3-Hydroxylase Mutants

The recombinant bacterial pellets of the recombinant bacteria Escherichia coli BL21/pET28a (+)-cis-P3H containing the wild-type enzyme and the recombinant bacteria containing mutants obtained in the step 3) of Example 1 were resuspended in 20 mM Tris-HCl buffer (pH 7.5), and cells were sonicated using an ultrasonic cell disruptor at 400 W power, with 2-second operation and 3-second interval; cell lysate was frozen and centrifuged in a refrigerated centrifuge at 4° C. and 12,000 r·min$^{-1}$ for 30 minutes, and a supernatant obtained after centrifugation was filtered through a 0.22 µm water filter membrane; purification was performed using a purifier of an AKTAxpress system, a 5 mL HisTrap HP column was used as a purification column; a column was rinsed with 20 mL ethanol and 40 mL deionized water at 4° C., and then equilibrated with 20 mL protein purification Solution A (150 mM NaCl, 20 mM Tris-HCl, pH 7.5); the cell lysate supernatant was filtered through a 0.22 µm filter membrane and then slowly loaded onto a chromatography column, the chromatography column was first washed with Elution Buffer 1 (80 mM imidazole, 20 mM Tris-HCl, 150 mM NaCl, pH 7.5, that is, 8% protein purification Solution B) to remove impurities, a target protein was then eluted with Elution Buffer 2 (250 mM imidazole, 20 mM Tris-HCl, 150 mM NaCl, pH 7.5, that is, 25% protein purification Solution B); and the eluted target protein was treated with a desalting column and a desalting buffer (10 mM Tris, 100 mM NaCl, pH 7.5) to obtain pure L-proline-3-hydroxylase.

Figure 2:
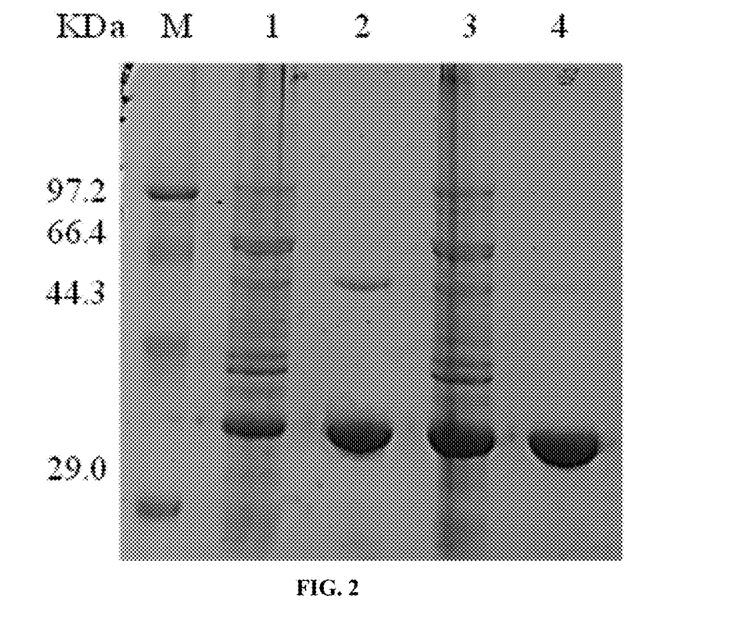
FIG. 2 shows SDS-PAGE electrophoresis results of an L-proline-3-hydroxylase mutant after purification, where M represents a protein molecular weight marker; 1 represents SDS-PAGE results of soluble fraction of wild-type L-proline-3-hydroxylase (WT); 2 represents SDS-PAGE results of pure WT; 3 represents SDS-PAGE results of soluble fraction of an L-proline-3-hydroxylase mutant R97M; and 4 represents SDS-PAGE results of pure R97M.

Purified enzyme solutions containing different positive mutants (FIG. 2) and the wild-type L-proline-3-hydroxylase were prepared, respectively.

Example 3: Enzyme Activity Assay

Specific steps were as follows:

Crude enzyme or pure protein (100 µL) was added to a reaction system (150 µL), a final reaction mixture was up to a volume of 250 µL, a final reaction system contained 10 mM substrate L-pipecolic acid, 10 mM α-ketoglutaric acid, 10 mM L-ascorbic acid, 1 mM FeSO$_4$·7H$_2$O, and 50 mM MES (pH 6.5); and the mixture was then incubated in a Thermomixer Comfort metal bath 17° C. and 1000 r· min$^{-1}$.

Specifically, the reaction under crude enzyme conditions was performed for 12 hours, the reaction under pure enzyme conditions was performed for 15 minutes, and a final protein concentration for the reaction under pure enzyme conditions was 0.5 mg·mL$^{-1}$.

The reaction was terminated by boiling, and the sample after the termination of reaction was analyzed by high-performance liquid chromatography (HPLC). One unit of enzyme activity was defined as an amount of enzyme required to produce 1 µmol of product per minute in a standard enzyme assay system.

The relative enzyme activity of the control R97M and the crude enzyme solutions containing different mutants at N43 site were tested, respectively, and results were shown in Table 2:

TABLE 2

Relative enzyme activity of crude enzyme solutions based on saturation mutants of N43 based on R97M

| Enzyme | Relative enzyme activity (%) | Enzyme | Relative enzyme activity (%) |
|---|---|---|---|
| R97M | 100.00 | R97M/N43S | 236.05 |
| R97M/N43G | 14.76 | R97M/N43T | 286.65 |
| R97M/N43A | 212.40 | R97M/N43C | 74.11 |
| R97M/N43V | 108.34 | R97M/N43Y | 13.11 |
| R97M/N43L | 14.38 | R97M/N43Q | 29.14 |
| R97M/N43I | 11.24 | R97M/N43D | 121.08 |
| R97M/N43M | 27.09 | R97M/N43E | 28.53 |
| R97M/N43W | 0.00 | R97M/N43K | 142.34 |
| R97M/N43F | 6.14 | R97M/N43R | 23.73 |
| R97M/N43P | 33.17 | R97M/N43H | 47.01 |

Relative enzyme activity of each mutant was calculated by setting the activity of R97M as 100%. As shown in Table 2, six positive mutants were obtained through saturation mutagenesis of N43 based on a R97M template: R97M/N43A, R97M/N43V, R97M/N43S, R97M/N43T, R97M/N43D and R97M/N43K, with relative enzyme activities being 212.40%, 108.34%, 236.05%, 286.65%, 121.08%, and 142.34%, respectively, corresponding to 2.12, 1.08, 2.36, 2.86, 1.21, and 1.42 times that of R97M. The specific enzyme activity of these six positive mutants at a pure enzyme level was detailed in Example 5.

Example 4: Comparison of Catalytic Performance Between Mutant R97M and Wild-Type (WT)

(1) Molar Yield (%)

Crude enzyme solutions (100 µL) of R97M and WT obtained in Example 2 were added to a reaction system (150 µL), and a final reaction system contained 10 mM substrate L-pipecolic acid, 10 mM α-ketoglutaric acid, 10 mM L-ascorbic acid, 1 mM FeSO$_4$·7H$_2$O, and 50 mM MES (pH 6.5); and reaction was carried out at 17° C. for 12 hours. The reaction was terminated by boiling, and the sample after the termination of reaction was analyzed by high-performance liquid chromatography (HPLC). An amount of product (2S,3R)-3-hydroxy-pipecolic acid was measured, and a corresponding molar yield was calculated.

Figure 3:
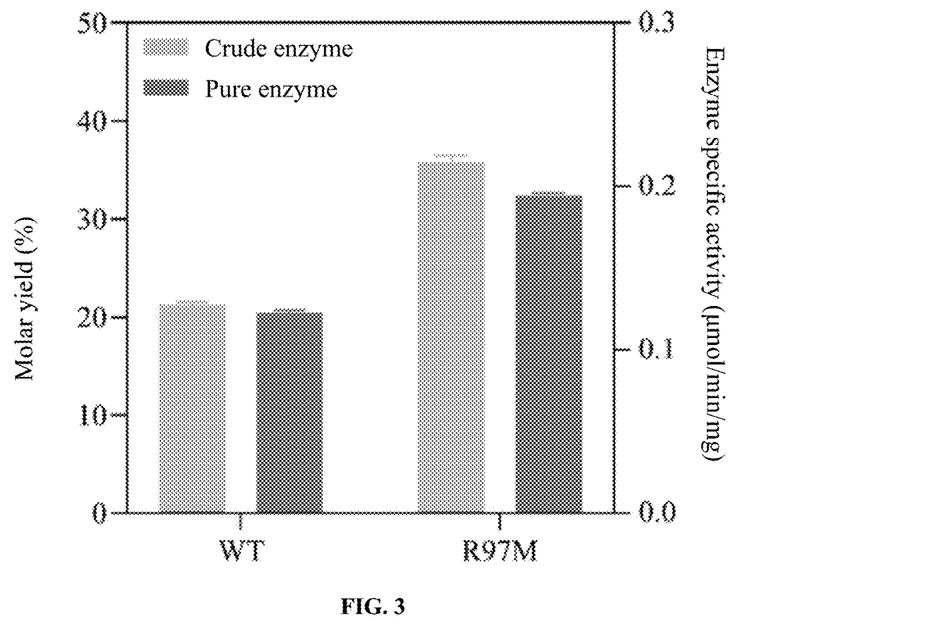
FIG. 3 shows catalytic performance of WT and R97M, where light-colored columns represent results under crude enzyme conditions, and a corresponding light-colored y-axis on a left represents a molar yield (%); the dark-colored columns represent results under pure enzyme conditions, and a corresponding dark-colored y-axis represents specific activity (μmol·min$^{-1}$·mg$^{-1}$).

As shown by a blue column in FIG. 3, compared with the wild-type enzyme, the L-proline-3-hydroxylase mutant R97M had a molar yield up to 36% under the enzyme activity assay conditions, which was 1.68 times that of the wild-type.

(2) Specific Activity ($\mu mol \cdot min^{-1} \cdot mg^{-1}$)

Purified enzymes (100 µL) of R97M and WT obtained in Example 2 were added to a reaction system (150 µL), and a final reaction system contained 10 mM substrate L-pipecolic acid, 10 mM α-ketoglutaric acid, 10 mM L-ascorbic acid, 1 mM $FeSO_4 \cdot 7H_2O$, and 50 mM MES (pH 6.5); reaction was carried out at 17° C. for 15 minutes, and a final protein concentration of pure enzymes was maintained at 0.50 mg ml-1. The reaction was terminated by boiling, and the sample after the termination of reaction was analyzed by high-performance liquid chromatography (HPLC). An amount of product was measured using the above detection method of (2S,3R)-3-hydroxy-pipecolic acid, and a corresponding specific activity was calculated.

As shown by a red column in FIG. 3, compared with the wild-type enzyme, the L-proline-3-hydroxylase mutant R97M had a specific activity up to 0.19 $\mu mol \cdot min^{-1} \cdot mg^{-1}$ under the enzyme activity assay conditions, which was 1.58 times that of the wild-type.

(3) Kinetic Parameters

Kinetic parameters ($K_m$ and $V_{max}$) were determined using a reaction mixture with a final volume of 250 µL. For the substrate L-pipecolic acid, a concentration of L-pipecolic acid under the standard enzyme activity conditions ranged from 0.30 to 25 mM. Similarly, a concentration of 2-OG ranged from 0.30 to 40 mM. The assay was performed three times, and a Michaelis-Menten model was fitted using GraphPad Prism. Results were shown in Table 3.

TABLE 3

Kinetic parameters of wild-type L-proline-3-hydroxylase and its mutant R97M

| Enzyme | Substrate | $K_m$ (mM) | $V_m$ ($\mu M \cdot min^{-1}$) | $k_{cat}$ ($min^{-1}$) | $k_{cat}/K_m$ ($min^{-1} mM^{-1}$) |
|---|---|---|---|---|---|
| cis-P3H (WT) | L-Pip | 10.27 ± 0.40 | 201.30 ± 2.00 | 12.23 ± 0.12 | 1.14 ± 0.03 |
|  | 2-OG | 0.76 ± 0.02 | 101.10 ± 1.50 | 6.14 ± 0.15 | 8.01 ± 0.38 |
| R97M | L-Pip | 6.83 ± 0.32 | 212.30 ± 3.50 | 13.82 ± 0.22 | 2.09 ± 0.06 |
|  | 2-OG | 1.46 ± 0.01 | 139.10 ± 1.23 | 9.05 ± 0.17 | 6.23 ± 0.32 |

The results showed that a Km value that R97M catalyzed the hydroxylation of L-pipecolic acid (6.83 mM) was lower than that of the WT enzyme (10.27 mM), indicating that R97M had an increased affinity for the substrate L-Pip. In addition, the catalytic efficiency kcat/Km of R97M (2.09 $min^{-1}$ $mM^{-1}$) was 1.83 times that of WT (1.14 $min^{-1}$ $mM^{-1}$).

Example 5: Comparison of Catalytic Performance Between R97M and Positive Mutants in an N43 Mutation Library The six positive mutants, that is, R97M/N43A, R97M/N43V, R97M/N43S, R97M/N43T, R97M/N43D and R97M/N43K, obtained in Example 3 were further studied, purification was performed according to the purification operation described in Example 2, and specific activities ($\mu mol \cdot min^{-1} \cdot mg^{-1}$) of these mutants were measured. Specific steps were as follows:

WT pure enzyme, R97M/N43A pure enzyme, R97M/N43V pure enzyme, R97M/N43S pure enzyme, R97M/N43D pure enzyme, and R97M/N43K pure enzyme (100 µL) were respectively added to a reaction mixture (150 µL), and a final reaction system contained 10 mM substrate L-pipecolic acid, 10 mM α-ketoglutaric acid, 10 mM L-ascorbic acid, 1 mM $FeSO_4 \cdot 7H_2O$, and 50 mM MES (pH 6.5); and reaction was carried out at 17° C. for 15 minutes; the reaction was terminated by boiling, and the sample after the termination of reaction was analyzed by high-performance liquid chromatography (HPLC). An amount of product (2S,3R)-3-hydroxy-pipecolic acid was measured using the above detection method of (2S,3R)-3-hydroxy-pipecolic acid, and a corresponding specific activity was calculated. Specific results were shown in Table 4. Final protein concentration=Initial protein concentration÷molar extinction coefficient× dilution factor.

TABLE 4

Specific activity of pure enzyme solutions based on positive mutants of N43 based on R97M

| Enzyme | Final protein concentration (mg · $mL^{-1}$) | Specific activity ($\mu mol \cdot min^{-1} \cdot mg^{-1}$) |
|---|---|---|
| cis-P3H(WT) | 0.56 | 0.12 |
| R97M | 0.55 | 0.19 |
| R97M/N43A | 0.50 | 0.45 |
| R97M/N43V | 0.48 | 0.24 |
| R97M/N43S | 0.43 | 0.34 |
| R97M/N43T | 0.37 | 0.46 |
| R97M/N43D | 0.43 | 0.32 |
| R97M/N43K | 0.69 | 0.21 |

Results showed that the specific activities of R97M/N43A, R97M/N43V, R97M/N43S, R97M/N43T, R97M/N43D and R97M/N43K were 2.37, 1.26, 1.79, 2.42, 1.68, and 1.11 times that of R97M, respectively, and 3.75, 0.20, 2.83, 3.83, 2.67, and 1.75 times that of the wild-type. It can be seen that R97M/N43T and R97M/N43A were both dominant mutants, with specific activities of 0.46 $\mu mol \cdot min^{-1} \cdot mg^{-1}$ and 0.45 $\mu mol \cdot min^{-1} \cdot mg^{-1}$, respectively. The following experiments were performed by only taking R97M/N43T as an example.

Example 6: Condition Optimization for Mutant R97M/N43T (1) Effect of Reaction Conditions on Yield of (2S,3R)-3-Hydroxypipecolic Acid
1) Temperature Optimization The R97M/N43T crude enzyme (100 µL) prepared in Example 2 was added to a reaction system (150 µL) for reaction, with specific operation as follows:

the R97M/N43T crude enzyme solution (100 µL) was added to a reaction system (150 µL), a final reaction system contained 10 mM substrate L-pipecolic acid, 10 mM α-ketoglutaric acid, 10 mM L-ascorbic acid, 1 mM $FeSO_4 \cdot 7H_2O$, and 50 mM MES (pH 6.5), a reaction mixture finally obtained had a total volume of 250 µL, and reaction was carried out for 12 hours at temperatures of 10° C., 17° C., 25° C., 30° C., 37° C., 45° C., and 55° C. Results were shown in FIG. 4.

Figure 4:
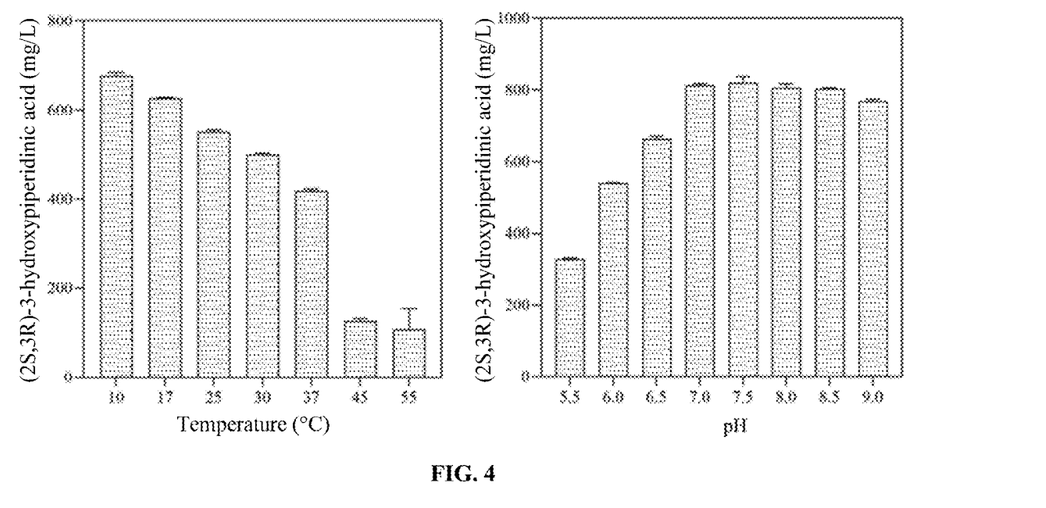
FIG. 4 shows effects of reaction conditions (temperature and pH) on yield of (2S,3R)-3-hydroxypipecolic acid.

The results indicated that R97M/N43T achieved a highest yield of (2S,3R)-3-hydroxypipecolic acid at 10° C., and yields of (2S,3R)-3-hydroxypipecolic acid at temperatures between 10-37° C. were significantly higher than those between 45-55° C.

2) pH Optimization

The R97M/N43T crude enzyme (100 µL) prepared in Example 2 was added to a reaction system (150 µL) for reaction, with specific operation as follows:

the R97M/N43T crude enzyme solution (100 μL) was added to a reaction system (150 μL), a final reaction system contained 10 mM substrate L-pipecolic acid, 10 mM α-ketoglutaric acid, 10 mM L-ascorbic acid, 1 mM $FeSO_4 \cdot 7H_2O$, pH values of MES buffer in the reaction system were set to 5.5, 6, 6.5 and 7, respectively, pH values of Tris-HCl buffer in the reaction system were set to 7, 7.5, 8, 8.5 and 9, respectively, a reaction mixture finally obtained had a total volume of 250 μL, and reaction was carried out for 12 hours at 17° C. Results were shown in FIG. 4.

The results indicated that (2S,3R)-3-hydroxypipecolic acid achieved a highest yield when pH was 7.5, and yields of (2S,3R)-3-hydroxypipecolic acid at pH between 7.0-9.0 were comparable, but relatively higher than those at pH between 5.5-6.5.

(2) Effect of Reaction Components on Yield of (2S,3R)-3-Hydroxypipecolic Acid

A specific method was the same as in step (1), the R97M/N43T crude enzyme (100 μL) prepared in Example 2 was added to the reaction mixture (150 μL), and reaction was carried out at 17° C. for 12 hours, except that: 1) a concentration of $Fe^{2+}$ in the final reaction system was adjusted to 0 mM, 0.05 mM, 0.10 mM, 0.25 mM, 0.50 mM, 1 mM, 2 mM, 3 mM and 4 mM; 2) a concentration of α-ketoglutaric acid (2-OG) in the final reaction system was adjusted to 0 mM, 5 mM, 10 mM, 15 mM, 20 mM, 25 mM, 30 mM, 35 mM and 40 mM; and 3) a concentration of L-ascorbic acid (Vc) in the final reaction system was adjusted to 0 mM, 2 mM, 5 mM, 10 mM, 15 mM, 20 mM, 25 mM and 30 mM; and other conditions were the same as those described in Example 3.

Figure 5:
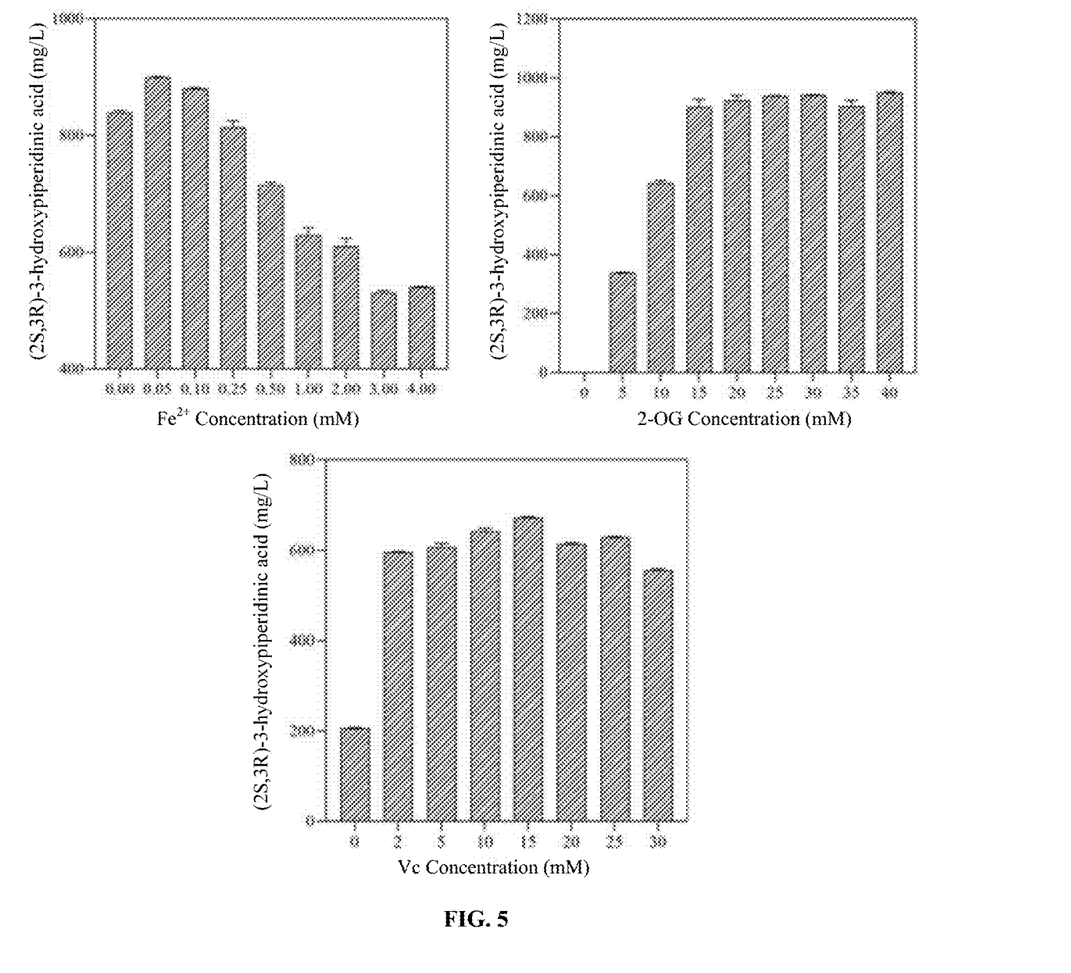
FIG. 5 shows effects of concentrations of $FeSO_4·7H_2O$, α-ketoglutaric acid, and L-ascorbic acid on the yield of (2S,3R)-3-hydroxypipecolic acid.

Results were shown in FIG. 5, and indicated that R97M/N43T achieved a highest yield of (2S,3R)-3-hydroxypipecolic acid when a concentration of $Fe^{2+}$ was 0.05 mM, a concentration of 2-OG was 30 mM and a concentration of Vc was 15 mM. Yields of (2S,3R)-3-hydroxypipecolic acid at a concentration of $Fe^{2+}$ between 0-0.5 mM were significantly higher than those between 1-4 mM, indicating that R97M/N43T was less tolerant to $Fe^{2+}$, and a higher concentration of $Fe^{2+}$ had a significant negative impact on catalytic activity of R97M/N43T. Moreover, dependence of R97M/N43T on $Fe^{2+}$ was not absolute, possibly because it has bound endogenous $Fe^{2+}$. Yields of (2S,3R)-3-hydroxypipecolic acid at a concentration of 2-OG between 15-40 mM were comparable but significantly higher than those at concentrations between 0-10 mM, in which case, a substrate concentration was 10 mM, so an addition amount of 2-OG should be greater than that of the substrate concentration. Further, no product was detected when a concentration of 2-OG was 0 mM, indicating an absolute dependence on 2-OG. Yields of (2S,3R)-3-hydroxypipecolic acid at a concentration of Vc between 2-30 mM were comparable but significantly higher than that at a concentrations of 0 mM, indicating that the addition of the antioxidant Vc could promote the reaction to some extent.

(3) Molar Yield of (2S,3R)-3-Hydroxypipecolic Acid Catalyzed by R97M/N43T Under Optimal Conditions According to the results of the optimization of conditions in (1) and (2) above, the optimized conditions were as follows:

The R97M/N43T crude enzyme (100 μL) prepared in Example 2 was added to a reaction system (150 μL) for reaction, with specific operation as follows:

the R97M/N43T crude enzyme (100 μL) was added to a reaction system (150 μL), a final reaction system contained 10 mM substrate L-pipecolic acid, 30 mM α-ketoglutaric acid, 15 mM L-ascorbic acid, 0.05 mM $FeSO_4 \cdot 7H_2O$, a reaction mixture finally obtained had a total volume of 250 μL, and reaction was carried out for 12 hours at a temperature of 10° C. and pH of 6.5.

The wild-type enzyme was taken as a control.

Evaluation was performed according to yields of (2S,3R)-3-hydroxypipecolic acid. The results showed that R97M/N43T achieved a molar yield of 8.82 mM at a substrate concentration of 10 mM under crude enzyme conditions, with a molar yield rate of 88%, and almost no substrate peak was detected, which was 4.11 times that of the wild-type enzyme (it had a molar yield rate of 21.40% and a yield of (2S,3R)-3-hydroxypipecolic acid up to 310 $mg \cdot L^{-1}$ under the initial reaction conditions as described in Item (1) of Example 4), in which case, the yield of (2S,3R)-3-hydroxypipecolic acid produced by R97M/N43T catalyzing L-pipecolic acid was 1278 $mg \cdot L^{-1}$.

Although the present disclosure has been disclosed as above in the form of preferred embodiments, it is not intended to limit the present disclosure. Those skilled in the art can make various modifications and variations without departing from the spirit and scope of the present disclosure. Therefore, the scope of protection of the present disclosure should be defined by the claims.

What is claimed is:

1. A mutated L-proline-3-hydroxylase comprising a variant of the wild-type L-proline-3-hydroxylase having SEQ ID NO:1, which comprises a substitution of the arginine corresponding to position 97 (R97) of SEQ ID NO:1 and a substitution of the asparagine corresponding to position 43 (N43) of SEQ ID NO: 1; wherein the amino acid substituted into the mutated L-proline-3-hydroxylase at position R97 is methionine, and wherein the amino acid substituted into the mutated L-proline-3-hydroxylase at position N43 is selected from the group consisting of threonine (T), alanine (A), valine (V), serine(S), aspartic acid (D), and lysine (K).

2. A microbial cell expressing the mutated L-proline-3-hydroxylase according to claim 1, or containing a gene encoding the mutated L-proline-3-hydroxylase, or containing a recombinant vector comprising a gene encoding the mutated L-proline-3-hydroxylase.

3. The microbial cell according to claim 2, wherein the microbial cell comprises a host cell and the host cell is bacteria or fungi.

4. The microbial cell according to claim 3, wherein the microbial cell comprises a host cell and the host cell is *Escherichia coli, Bacillus subtilis*, or yeast.

5. A method for preparing (2S,3R)-3-hydroxypipecolic acid, comprising: adding the mutated L-proline-3-hydroxylase according to claim 1 to a reaction system containing L-pipecolic acid, preparing and obtaining the (2S,3R)-3-hydroxypipecolic acid.

6. The method according to claim 5, wherein the reaction system comprises L-pipecolic acid, α-ketoglutaric acid, L-ascorbic acid, and $FeSO_4 \cdot 7H_2O$.

7. The method according to claim 6, wherein the method comprises: adding 100 μL of crude enzyme of the mutated L-proline-3-hydroxylase to 150 L of the reaction system and obtaining a final reaction system; wherein the final reaction system contains comprises 10 mM substrate L-pipecolic acid, 15 mM to 30 mM α-ketoglutaric acid is, 10 mM to 20 mM L-ascorbic acid, up to 0.10 mM $FeSO_4 \cdot 7H_2O$; the final reaction system has a total volume of 250 μL; and the reaction is carried out at 10° C. and pH of 6.5 for 12 hours.

8. The method according to claim 7, wherein the final reaction system comprises 10 mM substrate L-pipecolic acid, 30 mM α-ketoglutaric acid, 15 mM L-ascorbic acid, and 0.05 mM $FeSO_4 \cdot 7H_2O$; the final reaction system has a total volume of 250 μL; and the reaction is carried out at 10° C. and pH of 6.5 for 12 hours.

* * * * *

SEQUENCE LISTING

```
Sequence total quantity: 47
SEQ ID NO: 1           moltype = AA  length = 290
FEATURE                Location/Qualifiers
source                 1..290
                       mol_type = protein
                       organism = synthetic construct
SEQUENCE: 1
MRSHILGRIE LDQERLGRDL EYLATVPTVE EEYDEFSNGF WKNIPLYNAS GGSEDRLYRD    60
LEGSPAQPTK HAEQVPYLNE IITTVYNGER LQMARTRNLK NAVVIPHRDF VELDRELDQY   120
FRTHLMLEDS PLAFHSDDDT VIHMRAGEIW FLDAAAVHSA VNFAEFSRQS LCVDLAFDGA   180
FDEKEAFADA TVYAPNLSPD VRERKPFTKE REAGILALSG VIGRENFRDI LFLLSKVHYT   240
YDVHPGETFE WLVSVSKGAG DDKMVEKAER IRDFAIGARA LGERFSLTTW              290

SEQ ID NO: 2           moltype = DNA  length = 51
FEATURE                Location/Qualifiers
source                 1..51
                       mol_type = other DNA
                       organism = synthetic construct
SEQUENCE: 2
tgagttcagc aacggtttct ggaaacacat cccgctgtac aacgcgagcg g             51
```

```
SEQ ID NO: 3              moltype = DNA    length = 51
FEATURE                   Location/Qualifiers
source                    1..51
                          mol_type = other DNA
                          organism = synthetic construct
SEQUENCE: 3
ccgctcgcgt tgtacagcgg gatgtgtttc cagaaaccgt tgctgaactc a          51

SEQ ID NO: 4              moltype = AA     length = 290
FEATURE                   Location/Qualifiers
source                    1..290
                          mol_type = protein
                          organism = synthetic construct
SEQUENCE: 4
MRSHILGRIE LDQERLGRDL EYLATVPTVE EEYDEFSNGF WKTIPLYNAS GGSEDRLYRD    60
LEGSPAQPTK HAEQVPYLNE IITTVYNGER LQMARTMNLK NAVVIPHRDF VELDRELDQY   120
FRTHLMLEDS PLAFHSDDDT VIHMRAGEIW FLDAAAVHSA VNFAEFSRQS LCVDLAFDGA   180
FDEKEAFADA TVYAPNLSPD VRERKPFTKE REAGILALSG VIGRENFRDI LFLLSKVHYT   240
YDVHPGETFE WLVSVSKGAG DDKMVEKAER IRDFAIGARA LGERFSLTTW             290

SEQ ID NO: 5              moltype = AA     length = 290
FEATURE                   Location/Qualifiers
source                    1..290
                          mol_type = protein
                          organism = synthetic construct
SEQUENCE: 5
MRSHILGRIE LDQERLGRDL EYLATVPTVE EEYDEFSNGF WKAIPLYNAS GGSEDRLYRD    60
LEGSPAQPTK HAEQVPYLNE IITTVYNGER LQMARTMNLK NAVVIPHRDF VELDRELDQY   120
FRTHLMLEDS PLAFHSDDDT VIHMRAGEIW FLDAAAVHSA VNFAEFSRQS LCVDLAFDGA   180
FDEKEAFADA TVYAPNLSPD VRERKPFTKE REAGILALSG VIGRENFRDI LFLLSKVHYT   240
YDVHPGETFE WLVSVSKGAG DDKMVEKAER IRDFAIGARA LGERFSLTTW             290

SEQ ID NO: 6              moltype = AA     length = 290
FEATURE                   Location/Qualifiers
source                    1..290
                          mol_type = protein
                          organism = synthetic construct
SEQUENCE: 6
MRSHILGRIE LDQERLGRDL EYLATVPTVE EEYDEFSNGF WKVIPLYNAS GGSEDRLYRD    60
LEGSPAQPTK HAEQVPYLNE IITTVYNGER LQMARTMNLK NAVVIPHRDF VELDRELDQY   120
FRTHLMLEDS PLAFHSDDDT VIHMRAGEIW FLDAAAVHSA VNFAEFSRQS LCVDLAFDGA   180
FDEKEAFADA TVYAPNLSPD VRERKPFTKE REAGILALSG VIGRENFRDI LFLLSKVHYT   240
YDVHPGETFE WLVSVSKGAG DDKMVEKAER IRDFAIGARA LGERFSLTTW             290

SEQ ID NO: 7              moltype = AA     length = 290
FEATURE                   Location/Qualifiers
source                    1..290
                          mol_type = protein
                          organism = synthetic construct
SEQUENCE: 7
MRSHILGRIE LDQERLGRDL EYLATVPTVE EEYDEFSNGF WKSIPLYNAS GGSEDRLYRD    60
LEGSPAQPTK HAEQVPYLNE IITTVYNGER LQMARTMNLK NAVVIPHRDF VELDRELDQY   120
FRTHLMLEDS PLAFHSDDDT VIHMRAGEIW FLDAAAVHSA VNFAEFSRQS LCVDLAFDGA   180
FDEKEAFADA TVYAPNLSPD VRERKPFTKE REAGILALSG VIGRENFRDI LFLLSKVHYT   240
YDVHPGETFE WLVSVSKGAG DDKMVEKAER IRDFAIGARA LGERFSLTTW             290

SEQ ID NO: 8              moltype = AA     length = 290
FEATURE                   Location/Qualifiers
source                    1..290
                          mol_type = protein
                          organism = synthetic construct
SEQUENCE: 8
MRSHILGRIE LDQERLGRDL EYLATVPTVE EEYDEFSNGF WKDIPLYNAS GGSEDRLYRD    60
LEGSPAQPTK HAEQVPYLNE IITTVYNGER LQMARTMNLK NAVVIPHRDF VELDRELDQY   120
FRTHLMLEDS PLAFHSDDDT VIHMRAGEIW FLDAAAVHSA VNFAEFSRQS LCVDLAFDGA   180
FDEKEAFADA TVYAPNLSPD VRERKPFTKE REAGILALSG VIGRENFRDI LFLLSKVHYT   240
YDVHPGETFE WLVSVSKGAG DDKMVEKAER IRDFAIGARA LGERFSLTTW             290

SEQ ID NO: 9              moltype = AA     length = 290
FEATURE                   Location/Qualifiers
source                    1..290
                          mol_type = protein
                          organism = synthetic construct
SEQUENCE: 9
MRSHILGRIE LDQERLGRDL EYLATVPTVE EEYDEFSNGF WKKIPLYNAS GGSEDRLYRD    60
LEGSPAQPTK HAEQVPYLNE IITTVYNGER LQMARTMNLK NAVVIPHRDF VELDRELDQY   120
FRTHLMLEDS PLAFHSDDDT VIHMRAGEIW FLDAAAVHSA VNFAEFSRQS LCVDLAFDGA   180
FDEKEAFADA TVYAPNLSPD VRERKPFTKE REAGILALSG VIGRENFRDI LFLLSKVHYT   240
```

```
YDVHPGETFE WLVSVSKGAG DDKMVEKAER IRDFAIGARA LGERFSLTTW                290

SEQ ID NO: 10           moltype = DNA   length = 51
FEATURE                 Location/Qualifiers
source                  1..51
                        mol_type = other DNA
                        organism = synthetic construct
SEQUENCE: 10
tgaacgtctg caaatggcgc gtaccatgaa cctgaaaaac gctgttgtta t              51

SEQ ID NO: 11           moltype = DNA   length = 51
FEATURE                 Location/Qualifiers
source                  1..51
                        mol_type = other DNA
                        organism = synthetic construct
SEQUENCE: 11
ataacaacag cgttttttcag gttcatggta cgcgccattt gcagacgttc a             51

SEQ ID NO: 12           moltype = DNA   length = 51
FEATURE                 Location/Qualifiers
source                  1..51
                        mol_type = other DNA
                        organism = synthetic construct
SEQUENCE: 12
tgagttcagc aacggtttct ggaaaggcat cccgctgtac aacgcgagcg g              51

SEQ ID NO: 13           moltype = DNA   length = 51
FEATURE                 Location/Qualifiers
source                  1..51
                        mol_type = other DNA
                        organism = synthetic construct
SEQUENCE: 13
ccgctcgcgt tgtacagcgg gatgcctttc cagaaaccgt tgctgaactc a              51

SEQ ID NO: 14           moltype = DNA   length = 51
FEATURE                 Location/Qualifiers
source                  1..51
                        mol_type = other DNA
                        organism = synthetic construct
SEQUENCE: 14
tgagttcagc aacggtttct ggaaagcgat cccgctgtac aacgcgagcg g              51

SEQ ID NO: 15           moltype = DNA   length = 51
FEATURE                 Location/Qualifiers
source                  1..51
                        mol_type = other DNA
                        organism = synthetic construct
SEQUENCE: 15
ccgctcgcgt tgtacagcgg gatcgctttc cagaaaccgt tgctgaactc a              51

SEQ ID NO: 16           moltype = DNA   length = 51
FEATURE                 Location/Qualifiers
source                  1..51
                        mol_type = other DNA
                        organism = synthetic construct
SEQUENCE: 16
tgagttcagc aacggtttct ggaaagttat cccgctgtac aacgcgagcg g              51

SEQ ID NO: 17           moltype = DNA   length = 51
FEATURE                 Location/Qualifiers
source                  1..51
                        mol_type = other DNA
                        organism = synthetic construct
SEQUENCE: 17
ccgctcgcgt tgtacagcgg gataactttc cagaaaccgt tgctgaactc a              51

SEQ ID NO: 18           moltype = DNA   length = 51
FEATURE                 Location/Qualifiers
source                  1..51
                        mol_type = other DNA
                        organism = synthetic construct
SEQUENCE: 18
tgagttcagc aacggtttct ggaaactgat cccgctgtac aacgcgagcg g              51

SEQ ID NO: 19           moltype = DNA   length = 51
FEATURE                 Location/Qualifiers
source                  1..51
                        mol_type = other DNA
                        organism = synthetic construct
```

```
SEQUENCE: 19
ccgctcgcgt tgtacagcgg gatcagtttc cagaaaccgt tgctgaactc a          51

SEQ ID NO: 20           moltype = DNA   length = 51
FEATURE                 Location/Qualifiers
source                  1..51
                        mol_type = other DNA
                        organism = synthetic construct
SEQUENCE: 20
gagttcagca acggtttctg gaaaatcatc ccgctgtaca acgcgagcgg t          51

SEQ ID NO: 21           moltype = DNA   length = 51
FEATURE                 Location/Qualifiers
source                  1..51
                        mol_type = other DNA
                        organism = synthetic construct
SEQUENCE: 21
accgctcgcg ttgtacagcg ggatgatttt ccagaaaccg ttgctgaact c          51

SEQ ID NO: 22           moltype = DNA   length = 51
FEATURE                 Location/Qualifiers
source                  1..51
                        mol_type = other DNA
                        organism = synthetic construct
SEQUENCE: 22
gagttcagca acggtttctg gaaaatgatc ccgctgtaca acgcgagcgg t          51

SEQ ID NO: 23           moltype = DNA   length = 51
FEATURE                 Location/Qualifiers
source                  1..51
                        mol_type = other DNA
                        organism = synthetic construct
SEQUENCE: 23
accgctcgcg ttgtacagcg ggatcatttt ccagaaaccg ttgctgaact c          51

SEQ ID NO: 24           moltype = DNA   length = 51
FEATURE                 Location/Qualifiers
source                  1..51
                        mol_type = other DNA
                        organism = synthetic construct
SEQUENCE: 24
tgagttcagc aacggtttct ggaaatggat cccgctgtac aacgcgagcg g          51

SEQ ID NO: 25           moltype = DNA   length = 51
FEATURE                 Location/Qualifiers
source                  1..51
                        mol_type = other DNA
                        organism = synthetic construct
SEQUENCE: 25
ccgctcgcgt tgtacagcgg gatccatttc cagaaaccgt tgctgaactc a          51

SEQ ID NO: 26           moltype = DNA   length = 51
FEATURE                 Location/Qualifiers
source                  1..51
                        mol_type = other DNA
                        organism = synthetic construct
SEQUENCE: 26
tgagttcagc aacggtttct ggaaattcat cccgctgtac aacgcgagcg g          51

SEQ ID NO: 27           moltype = DNA   length = 51
FEATURE                 Location/Qualifiers
source                  1..51
                        mol_type = other DNA
                        organism = synthetic construct
SEQUENCE: 27
ccgctcgcgt tgtacagcgg gatgaatttc cagaaaccgt tgctgaactc a          51

SEQ ID NO: 28           moltype = DNA   length = 51
FEATURE                 Location/Qualifiers
source                  1..51
                        mol_type = other DNA
                        organism = synthetic construct
SEQUENCE: 28
tgagttcagc aacggtttct ggaaaccgat cccgctgtac aacgcgagcg g          51

SEQ ID NO: 29           moltype = DNA   length = 51
FEATURE                 Location/Qualifiers
source                  1..51
                        mol_type = other DNA
```

```
                                organism = synthetic construct
SEQUENCE: 29
ccgctcgcgt tgtacagcgg gatcggtttc cagaaaccgt tgctgaactc a              51

SEQ ID NO: 30           moltype = DNA   length = 51
FEATURE                 Location/Qualifiers
source                  1..51
                        mol_type = other DNA
                        organism = synthetic construct
SEQUENCE: 30
gagttcagca acggtttctg gaaaagcatc ccgctgtaca acgcgagcgg t              51

SEQ ID NO: 31           moltype = DNA   length = 51
FEATURE                 Location/Qualifiers
source                  1..51
                        mol_type = other DNA
                        organism = synthetic construct
SEQUENCE: 31
accgctcgcg ttgtacagcg ggatgctttt ccagaaaccg ttgctgaact c              51

SEQ ID NO: 32           moltype = DNA   length = 51
FEATURE                 Location/Qualifiers
source                  1..51
                        mol_type = other DNA
                        organism = synthetic construct
SEQUENCE: 32
gagttcagca acggtttctg gaaaaccatc ccgctgtaca acgcgagcgg t              51

SEQ ID NO: 33           moltype = DNA   length = 51
FEATURE                 Location/Qualifiers
source                  1..51
                        mol_type = other DNA
                        organism = synthetic construct
SEQUENCE: 33
accgctcgcg ttgtacagcg ggatggtttt ccagaaaccg ttgctgaact c              51

SEQ ID NO: 34           moltype = DNA   length = 51
FEATURE                 Location/Qualifiers
source                  1..51
                        mol_type = other DNA
                        organism = synthetic construct
SEQUENCE: 34
tgagttcagc aacggtttct ggaaatgcat cccgctgtac aacgcgagcg g              51

SEQ ID NO: 35           moltype = DNA   length = 51
FEATURE                 Location/Qualifiers
source                  1..51
                        mol_type = other DNA
                        organism = synthetic construct
SEQUENCE: 35
ccgctcgcgt tgtacagcgg gatgcatttc cagaaaccgt tgctgaactc a              51

SEQ ID NO: 36           moltype = DNA   length = 51
FEATURE                 Location/Qualifiers
source                  1..51
                        mol_type = other DNA
                        organism = synthetic construct
SEQUENCE: 36
tgagttcagc aacggtttct ggaaatacat cccgctgtac aacgcgagcg g              51

SEQ ID NO: 37           moltype = DNA   length = 51
FEATURE                 Location/Qualifiers
source                  1..51
                        mol_type = other DNA
                        organism = synthetic construct
SEQUENCE: 37
ccgctcgcgt tgtacagcgg gatgtatttc cagaaaccgt tgctgaactc a              51

SEQ ID NO: 38           moltype = DNA   length = 51
FEATURE                 Location/Qualifiers
source                  1..51
                        mol_type = other DNA
                        organism = synthetic construct
SEQUENCE: 38
tgagttcagc aacggtttct ggaaacagat cccgctgtac aacgcgagcg g              51

SEQ ID NO: 39           moltype = DNA   length = 51
FEATURE                 Location/Qualifiers
source                  1..51
```

```
                    mol_type = other DNA
                    organism = synthetic construct
SEQUENCE: 39
ccgctcgcgt tgtacagcgg gatctgtttc cagaaaccgt tgctgaactc a            51

SEQ ID NO: 40       moltype = DNA  length = 51
FEATURE             Location/Qualifiers
source              1..51
                    mol_type = other DNA
                    organism = synthetic construct
SEQUENCE: 40
tgagttcagc aacggtttct ggaaagacat cccgctgtac aacgcgagcg g            51

SEQ ID NO: 41       moltype = DNA  length = 51
FEATURE             Location/Qualifiers
source              1..51
                    mol_type = other DNA
                    organism = synthetic construct
SEQUENCE: 41
ccgctcgcgt tgtacagcgg gatgtctttc cagaaaccgt tgctgaactc a            51

SEQ ID NO: 42       moltype = DNA  length = 51
FEATURE             Location/Qualifiers
source              1..51
                    mol_type = other DNA
                    organism = synthetic construct
SEQUENCE: 42
tgagttcagc aacggtttct ggaaagaaat cccgctgtac aacgcgagcg g            51

SEQ ID NO: 43       moltype = DNA  length = 51
FEATURE             Location/Qualifiers
source              1..51
                    mol_type = other DNA
                    organism = synthetic construct
SEQUENCE: 43
ccgctcgcgt tgtacagcgg gatttctttc cagaaaccgt tgctgaactc a            51

SEQ ID NO: 44       moltype = DNA  length = 51
FEATURE             Location/Qualifiers
source              1..51
                    mol_type = other DNA
                    organism = synthetic construct
SEQUENCE: 44
agttcagcaa cggtttctgg aaaaaaatcc cgctgtacaa cgcgagcggt g            51

SEQ ID NO: 45       moltype = DNA  length = 51
FEATURE             Location/Qualifiers
source              1..51
                    mol_type = other DNA
                    organism = synthetic construct
SEQUENCE: 45
caccgctcgc gttgtacagc gggatttttt tccagaaacc gttgctgaac t            51

SEQ ID NO: 46       moltype = DNA  length = 51
FEATURE             Location/Qualifiers
source              1..51
                    mol_type = other DNA
                    organism = synthetic construct
SEQUENCE: 46
tgagttcagc aacggtttct ggaaacgtat cccgctgtac aacgcgagcg g            51

SEQ ID NO: 47       moltype = DNA  length = 51
FEATURE             Location/Qualifiers
source              1..51
                    mol_type = other DNA
                    organism = synthetic construct
SEQUENCE: 47
ccgctcgcgt tgtacagcgg gatacgtttc cagaaaccgt tgctgaactc a            51
```